United States Patent [19]
Gupta

[11] Patent Number: 5,718,693
[45] Date of Patent: Feb. 17, 1998

[54] HEMATOMA PREVENTION APPARATUS AND METHOD

[76] Inventor: Mukesh Gupta, 6958 Hiland Park Dr., Nashville, Tenn. 37205

[21] Appl. No.: 519,740

[22] Filed: Aug. 28, 1995

[51] Int. Cl.$^6$ ............................................. A61M 5/00
[52] U.S. Cl. ..................................... 604/264; 604/171
[58] Field of Search ............................... 604/264, 164, 604/171, 280

[56] References Cited

U.S. PATENT DOCUMENTS

| | | | |
|---|---|---|---|
| 5,158,540 | 10/1992 | Wijay et al. | 604/43 |
| 5,158,545 | 10/1992 | Trudell et al. | |
| 5,509,909 | 4/1996 | Moy | 604/264 |
| 5,542,936 | 8/1996 | Razi | 604/264 |

OTHER PUBLICATIONS

Duthie; Medical Intelligence, Drainage of the Abdomen; vol. 287, No. 21, pp. 1081–1083.

Hanna; Efficiency of Peritoneal Drainage; Surgery, Gynecology & Obstetrics; Nov., 1970; pp. 983–985.

*Primary Examiner*—Michael Powell Buiz
*Assistant Examiner*—N. Kent Gring
*Attorney, Agent, or Firm*—Hovey, Williams, Timmons & Collins

[57] ABSTRACT

Hematoma-preventing cannula assemblies (36, 79) are provided which comprise an elongated cannula (10, 80) preferably equipped with a blood-conveying sleeve (38) positioned about the cannula shaft (12, 82) and presenting a plurality of axial blood flow passageways (46). The cannula (10, 80) is inserted in the usual fashion with the distal end thereof passing through an opening (22a) of a blood vessel (14) and the proximal end outside the patient's body; this creates a gap (32) between the exterior surface of the cannula shaft (12, 82) and the adjacent margins of the opening (22a). The sleeve (38) is percutaneously located with the inner end (42) thereof adjacent opening (22a) and gap (32), whereas the outer end (40) of the sleeve (38) is located adjacent the proximal end of the cannula (10, 80). In use, seepage flow of blood through gap (32) exteriorly of the cannula shaft (12, 82) is directed through the passageways (46) and thus cannot collect in tissue adjacent the vessel (14) to form a hematoma. In an alternative embodiment, a diameter expansion cannula (80) is provided together with a tubular dilator (88). After positioning of the cannula (80), the dilator (88) is used to radially expand the diameter of cannula shaft (82), thus partially or completely closing the gap (32) and thereby preventing hematoma formation.

15 Claims, 3 Drawing Sheets

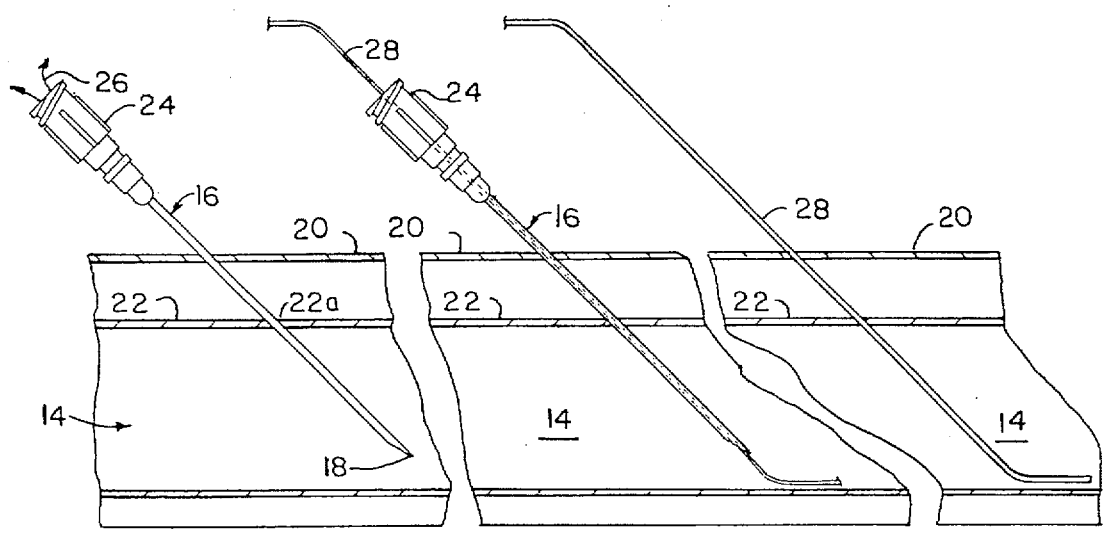
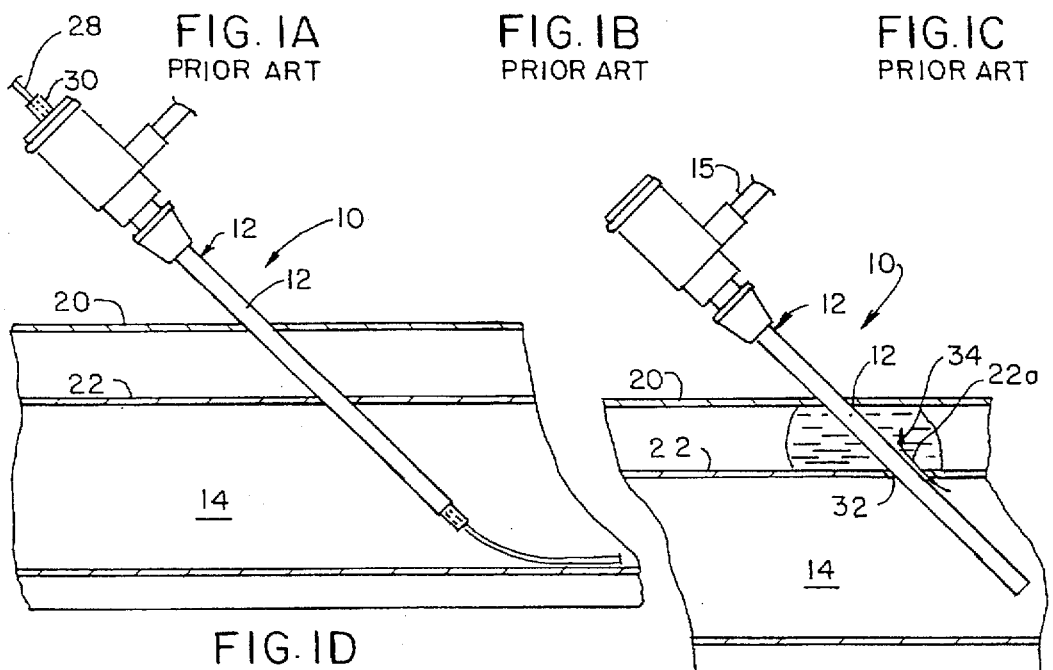
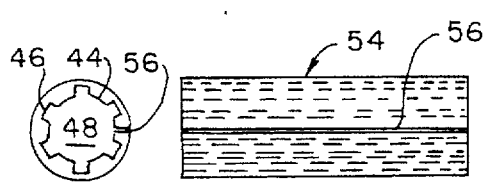
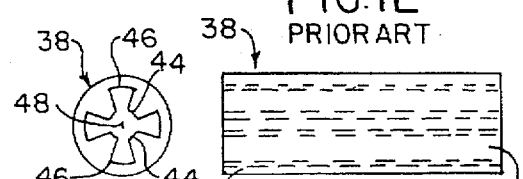
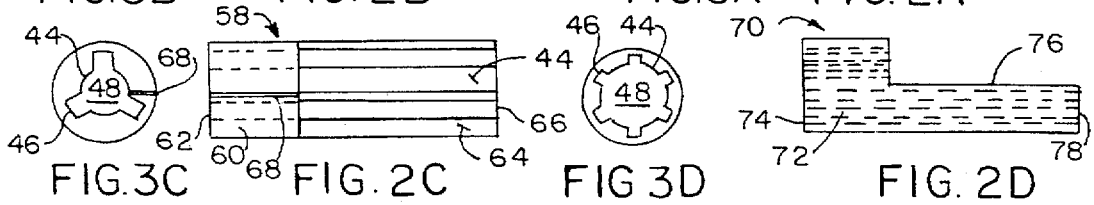

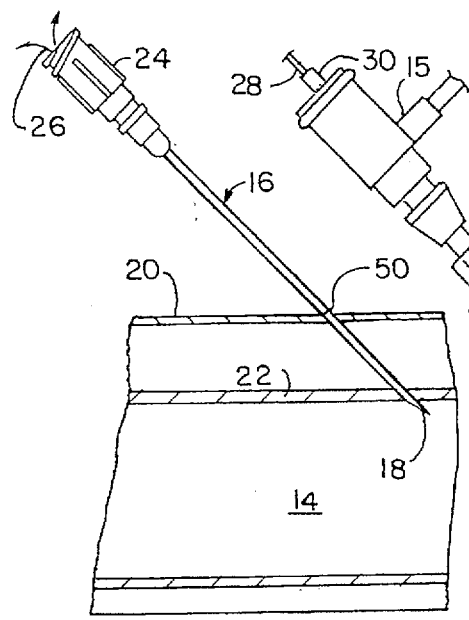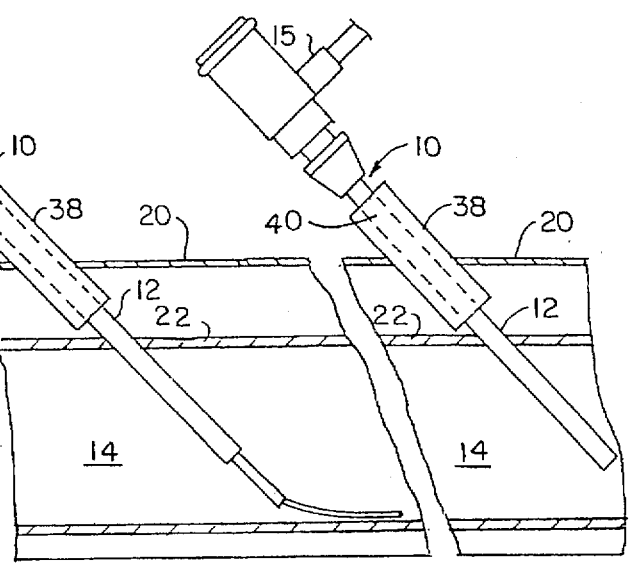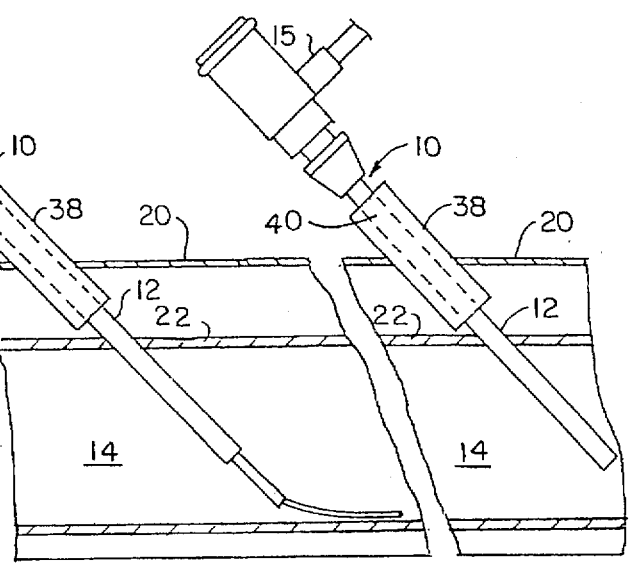
FIG. 4A    FIG. 4B    FIG. 4C
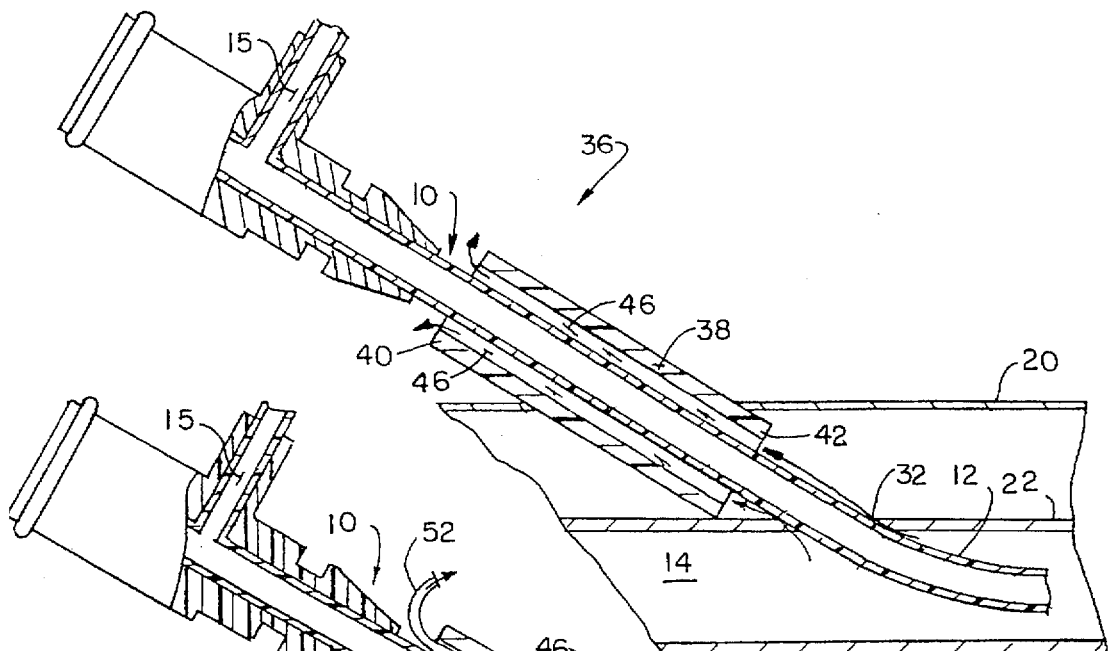
FIG. 5
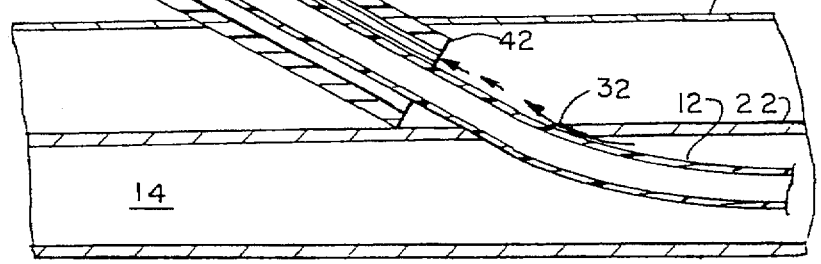
FIG. 6

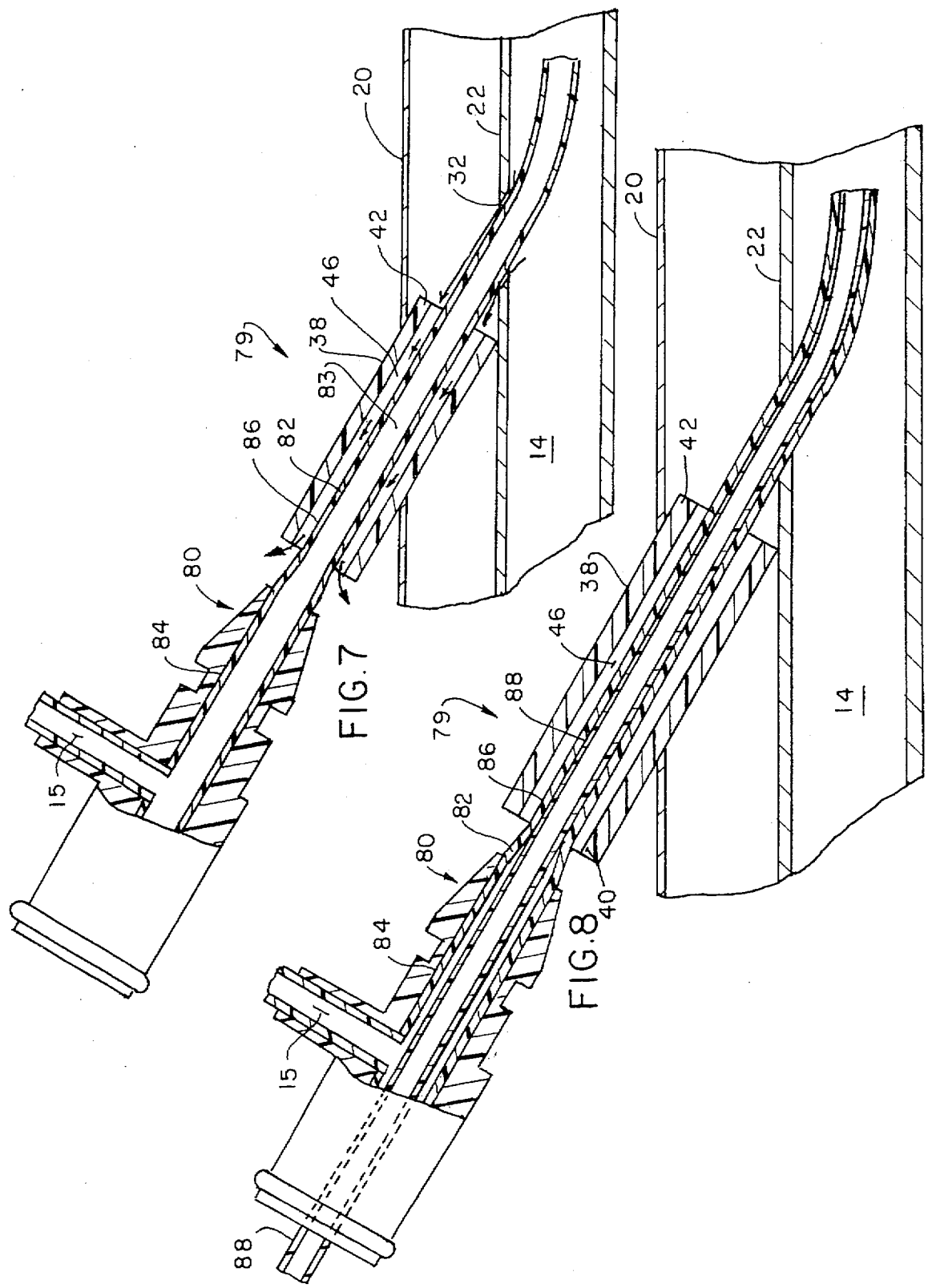

HEMATOMA PREVENTION APPARATUS AND METHOD

BACKGROUND OF THE INVENTION

1. Field of the Invention

The present invention relates to hematoma-preventing percutaneous cannula assemblies used in various procedures wherein subcutaneous blood vessels are cannulized. More particularly, the invention pertains to such cannula assemblies including a percutaneous cannula equipped with an exterior tubular percutaneous sleeve having one or more axially extending blood flow passageways formed therein; in use, the seepage flow of blood escaping a vessel around the cannula body is directed out of the patient's body to thus prevent hematoma formation. In another embodiment, a flexible cannula is equipped with an inner dilator for radial expansion of the cannula in order to minimize escape of blood from the vessel around the cannula body.

2. Description of the Prior Art

Many common medical procedures require the cannulation of blood vessels. For example, it may be necessary to extract blood samples or to administer medicaments into the blood stream.

Cannulation procedures of these types generally require that a percutaneous tubular cannula be inserted through a patient's skin and into a subcutaneous blood vessel. This of course necessitates that an incision or hole be made in the defining wall of the blood vessel in order to accommodate the cannula body. Various methods exist for accomplishing this task. For example, one known method involves inserting a rigid, hollow needle through a patient's skin and into a blood vessel, then passing a guide wire through the needle, withdrawing the needle, passing a cannula over the guide wire, and, finally, removing the guide wire. After removal of the guide wire, the emplaced cannula provides an unobstructed passageway to the blood vessel.

Another known method involves inserting a combined rigid needle and cannula simultaneously into and through the skin and blood vessel wall. Once the cannula is positioned, the needle is removed leaving the cannula in place for use.

The holes formed in the blood vessel walls, however, tend to be larger than the diameter of the cannula. Therefore, gaps exist between the outer surface of the cannula and the adjacent edge of the incision or hole in the blood vessel wall. Due to these gaps, blood may begin to escape or seep from the vessel and leak into the surrounding tissue, resulting in formation of a hematoma. Hematomas can be dangerous, inasmuch as they have a tendency to compress the wall of the adjacent blood vessel which in turn may lead to vessel collapse and obliteration of the lumen, stopping the flow of blood.

The size and pressure conditions created by a hematoma are dictated by the size of the gaps between the exterior surface of the inserted cannula and the adjacent vessel wall, and the length of time the cannula is in place. Gaps, therefore, have the most pronounced effect on hematoma formation during lengthy medical procedures where the cannula remains in place for extended periods. Coronary stent placement is one such lengthy procedure requiring cannulation of the femoral artery for a prolonged time period. As a result, even the smallest of gaps may result in the formation of hematomas which may provide sufficient pressure to collapse the femoral artery. Such a collapse is very dangerous, and can effectively cut off the blood supply to the leg. Such a condition would then lead, if it is not arrested, to necrosis of the leg muscles, possibly requiring amputation of the leg.

Various methods exist for reducing and eliminating the gaps between the cannula shaft and the adjacent edges of the hole in the blood vessel. For example, it is known to replace the shaft of the cannula with a shaft having a larger diameter in order to minimize the gaps and thus stop the flow of escaping blood and the consequent formation of a hematoma. Cannula replacement, however, results in discomfort to the patient and may further injure the blood vessel.

It is also known to provide a radially expandable cannula shaft which can be expanded for enlargement and repair of diseased vessels. Such diameter expansion cannulas include a shaft constructed of a resilient braided material which is inserted into a sheath sized to elongate and narrow the diameter of the shaft. Once the cannula is inserted into the vessel, the sheath may be removed, thereby allowing the shaft to expand to its original precompressed diameter.

Once a hematoma has formed, it is desirable to reduce its size and eventually evacuate the hematoma altogether. One known method involves surgically draining the hematoma by making an incision in the tissues overlaying the hematoma and evacuating the hematoma. Of course, surgical drainage results in trauma and risk of infection in addition to that required to perform cannulation and catheterization procedures.

Various devices are known for drainage of abdominal fluids. For example, it is known to drain an abdomen by inserting an elongated tube having open, distal and proximal ends into the abdomen so that the distal end is within the body adjacent the fluid collection site and the proximal end extends out of the body. Such a drain device, often referred to as a Penrose drain, allows the collected fluids to drain from the abdomen through a combination of capillary attraction and gravity.

There is accordingly a real and unsatisfied need in the art for improved cannula assemblies designed to eliminate or at least minimize the formation of hematomas resulting from cannulation of blood vessels.

SUMMARY OF THE INVENTION

The present invention overcomes the problems noted above and provides cannula assemblies specially designed to eliminate or minimize the formation of hematomas occasioned by cannulation procedures. More particularly, the invention pertains to cannula assemblies including an elongated percutaneous cannula adapted for insertion through a patient's skin and into a subcutaneous blood vessel. An elongated sleeve is positioned about a portion of the cannula with the inner end of the sleeve adjacent the blood vessel and extending outwardly through the patient's skin. This sleeve includes structure defining at least one elongated, axially extending blood flow passageway between the inner and outer sleeve ends for permitting seepage flow of blood escaping from the vessel through the sleeve passageway and out of the patient's body in order to prevent the formation of hematomas.

In preferred forms, the sleeve is configured to present a central bore with a plurality of circumferentially spaced recesses about the bore and along the length of the sleeve defining a corresponding plurality of blood flow passageways. To this end, the preferred sleeves are formed of flexible synthetic resin material and may include an elongated, axially extending, joint-defining slit to assist in placement of the sleeve on the cannula shaft. In other embodiments, the proximal ends of the sleeves of the invention may be equipped with arcuate segments which support the cannula body and include structure defining a continuation of the sleeve blood flow passageway(s). In order to assist in blood drainage, the sleeves of the invention may be equipped with suction tubes adapted for connection to a vacuum source. After lengthy procedures, the anesthetic administered prior to making the initial incision in the patient's body is usually no longer effective. Therefore, the sleeves may also be equipped with an anesthetic injecting tube. By providing such a tube, an anesthetic may be administered without the painful use of needles.

In another aspect of the invention, the hematoma-preventing cannula assembly comprises an elongated, flexible, radially expandable percutaneous cannula, together with a tubular dilator positioned within the cannula and radially expanding the latter at a point adjacent a cannulized blood vessels. Such radial expansion tends to close the gap between the exterior surface of the cannula shaft and the blood vessel wall, thereby tending to lessen the seepage flow of blood escaping from the blood vessel.

BRIEF DESCRIPTION OF THE INVENTION

FIG. 1A is a generally schematic view illustrating the first step in a prior art cannulation procedure wherein a rigid tubular needle is inserted through the patient's skin and into a blood vessel;

FIG. 1B is a view similar to that of FIG. 1A but illustrating the second step in the cannulation procedure wherein a guide wire is passed through the inserted needle;

FIG. 1C is a view similar to that of FIG. 1B depicting the next step in the procedure wherein the needle is removed, leaving the guide wire in place;

FIG. 1D is a schematic view similar to that of FIG. 1C but showing placement of a cannula over the guide wire;

FIG. 1E is a view similar to that of FIG. 1D, but showing the cannula in place with the guide wire removed and also depicting the formation of a hematoma resulting from escape of blood from the vessel through the gap between the cannula body and the vessel wall;

FIG. 2A is a side view of a cannula sleeve in accordance with the invention with the location of internal blood flow passageways being depicted in phantom;

FIG. 2B is a view similar to that of FIG. 2A but illustrating another sleeve embodiment;

FIG. 2C is a top view of another cannula sleeve in accordance with the invention;

FIG. 2D is a side view of another cannula sleeve in accordance with the invention;

FIG. 3A is an end elevational view of the sleeve depicted in FIG. 2A;

FIG. 3B is an end elevational view of the sleeve depicted in FIG. 2B;

FIG. 3C is an end elevational view of the sleeve depicted in FIG. 2C;

FIG. 3D is an end elevational view of the sleeve depicted in FIG. 2D;

FIG. 4A is a generally schematic, fragmentary side view illustrating the first step in the preferred cannulation procedure of the invention, wherein a rigid tubular needle is inserted through the patient's skin and through a subcutaneous blood vessel wall;

FIG. 4B is a view similar to that of FIG. 4A but illustrating the cannulation procedure after insertion of a guide wire through the rigid needle and removal of the needle and placement of a cannula assembly in accordance with the invention over the guide wire;

FIG. 4C is a view similar to that of FIG. 4B but illustrating the cannula assembly of the invention fully in place with the distal end thereof within the blood vessel;

FIG. 5 is an enlarged, fragmentary view in partial vertical section illustrating the emplaced cannula assembly of the invention in operation wherein flow of escaping blood from the blood vessel is directed extracorporeally through the cannula assembly sleeve;

FIG. 6 is a view similar to that of FIG. 5 but illustrating the use of a suction tube carried by the exterior cannula assembly sleeve for assisting in drainage of escaping blood;

FIG. 7 is a view similar to that of FIG. 5 but illustrating another embodiment of the invention making use of a radially expandable cannula; and FIG. 8 is a view similar to that of FIG. 7 but illustrating the insertion of a cannula-expanding dilator into the cannula lumen in order to expand the cannula shaft and assist in the prevention of seepage flow of blood from the blood vessel.

DETAILED DESCRIPTION OF THE PREFERRED EMBODIMENT

FIGS. 1A–1E depict a known method of cannulation, wherein cannula 10 having elongated hollow shaft 12 is introduced into blood vessel 14 of the body of a patient. Cannula 10 is a conventional device having side arm 15, depicted as a tube, for use in cannulation or catheterization procedures where a passageway is created to blood vessel 14. Vessel 14 may be a blood vein or an artery, such as the femoral artery in the leg.

In broad terms, an incision is made through skin layer 20 of the patient's body adjacent to vessel 14, and skin layer 20 and the subcutaneous tissue are spread apart by a forceps (not shown). Next, a hollow needle 16 having tip 18 is inserted into the patient's body through the incision until tip 18 punctures vessel wall 22, creating a hole 22a through wall 22. Generally, proper placement of needle 16 is confirmed by passage of blood out of the proximal hub 24 of the needle, as illustrated at 26. In the next step (FIG. 1B), guide wire 28 is inserted through needle 16, and the latter is removed leaving guide wire 28 in place. Thereupon, cannula 10 equipped with hollow internal dilator 30 is inserted over guide wire 28 until the distal end of shaft 12 is within vessel 14. Guide wire 28 and dilator 30 are then removed so that cannula 10 is ready for use.

Referring to FIG. 1E, it will be observed that the conventional cannulation procedure produces a gap 32 between the edge of the hole 22a through vessel wall 22 and the exterior surface of shaft 12. As a result, blood escapes from vessel 14 through gap 32, collecting in the adjacent tissues to form hematoma 34.

Referring now to FIG. 5, a preferred cannula assembly 36 in accordance with the invention is illustrated in use. Broadly speaking, the assembly 36 includes, in addition to the cannula 10 described above, an elongated sleeve 38. The sleeve 38 is positioned around and is supported by shaft 12 of cannula 10. Referring to FIGS. 2A and 3A, the sleeve 38 presents opposed, open proximal and distal ends 40 and 42, and includes an inner bore-defining surface presenting axially extending, circumferentially spaced ridges 44 and intervening, axially extending channels or recesses 46. As best illustrated in FIG. 3A, the sleeve 38 thus defines a central cannula shaft-receiving bore 48 defined by the spaced ridges 44. The bore 48 is configured to accommodate and frictionally engage the outer surface of shaft 12 of cannula 10 as best seen in FIG. 5.

Sleeve 38 is preferably constructed of flexible synthetic resin material, such as medical grade silicone. Alternatively, sleeve 38 may be constructed of various other materials, such as a relatively rigid plastic or metal.

In operation, sleeve 38 is first positioned around shaft 12 prior to insertion of shaft 12 into the body of the patient. It will be appreciated that the incision in the patient's body may be spread apart by forceps as shaft 12 is placed over guide wire 28 in order to facilitate placement of assembly 36. Sleeve 38 is of sufficient length so that when assembly 36 is in place and ready for use, distal end 42 is adjacent hole 22a and proximal end 40 is located outside the patient's body.

The proper length of sleeve 38 is determined during the cannulation procedure. In a preferred method, needle 16 is used to measure the distance between layer 20 and hole 22a. Referring to FIG. 4A, once tip 18 has punctured wall 22, as indicated by blood passing through needle hub 24, a mark is made on the shaft of needle 16 adjacent skin layer 20, as illustrated at 50. After guide wire 28 has been inserted through needle 16, and needle 16 has been removed, the distance between tip 18 and the mark at 50 is measured. The proper length of sleeve 38 to be used is then determined by adding approximately 5 mm to this measurement. Sleeve 38 is then cut to this length and positioned on the cannula shaft 12. In an alternative method, the measurement may be taken directly by using a needle having measurement markings along its shaft.

Once the distal end of shaft 12 is properly positioned within vessel 14, sleeve 38 directs blood escaping from vessel 14 through gap 32 along channels 46 to proximal end 40. It will be appreciated by those skilled in the art that the blood is caused to move along channels 46 due to capillary attraction and the force caused by the difference in pressure within the tissues surrounding gap 32 and the ambient pressure outside of the patient's body. As the blood is directed away from the tissues surrounding gap 32, formation of a hematoma is thus prevented.

After the blood reaches proximal end 40, it may be removed by any known means, such as by suction or by sponge. For example, FIG. 6 shows tube 52 inserted into one of channels 46. Tube 52 is connected with a source of suction (not shown) to assist in removal of blood from sleeve 38. Multiple tubes inserted into several of channels 46 may also be used.

During lengthy procedures it is common for the anesthetic administered to the patient prior to the initial incision to be no longer effective, thereby causing pain during removal of assembly 36 from the patient's body. Therefore, in an alternative form, tube 52 is connected with a source of an anesthetic (not shown). It will be appreciated that connecting tube 52 with an anesthetic source allows the area adjacent hole 22a to be anesthetized in order to reduce the pain associated with removing assembly 36, and does not require the use of a needle.

Alternative embodiments of the sleeve are shown in FIGS. 2B-D and 3B-D. For example, FIGS. 2B and 3B depict sleeve 54 which includes slit 56 extending along its length defining a pair of abutting edges. Sleeve 54 is constructed of a flexible material, such as a flexible synthetic resin. It will be appreciated that the edges along slit 56 may be pulled apart thereby allowing sleeve 54 to be positioned around shaft 12 after cannulation when cannula 10 is already in position.

FIGS. 2C and 3C depict sleeve 58 which includes first portion 60 defining a substantially circular cross-sectional shape adjacent distal end 62, and second portion 64 defining a semicircular cross-sectional shape adjacent proximal end 66. Slit 68 extends along first portion 60 defining a pair of edges. It will be appreciated that second portion 64 includes channels 46, and thus still functions to direct blood escaping from vessel 14 through gap 32 to proximal end 66. Once the blood reaches proximal end 66, it may be removed as stated above.

FIGS. 2D and 3D depict yet another embodiment. Sleeve 70 includes first portion 72 defining a substantially circular cross-sectional shape adjacent distal end 74, and second portion 76 defining a semicircular cross-sectional shape adjacent proximal end 78. Sleeve 70 does not include a slit as does sleeve 58, therefore, sleeve 70 must be positioned prior to cannulation. Once cannula 10 is in place, channels 46 direct blood to proximal end 78 where it may be removed as stated above.

Referring now to FIGS. 7 and 8, an alternative hematoma-preventing cannula assembly 79 is depicted which includes a diameter expansion cannula 80 having hollow shaft 82 defining a bore 83 presenting an upper portion 84 and lower portion 86. The diameter of upper portion 84 is slightly larger than the diameter of lower portion 86. For example, diameter of upper portion 84 is between about 5-50%, and preferably about 20%, larger than the diameter of lower portion 86. Shaft 82 is constructed of flexible synthetic resin material.

Cannula 80 further includes dilator 88 which may be inserted through the bore of shaft 82 after cannlation. Tubular dilator 88 defines an exterior diameter which is between about 5-20%, and preferably about 10%, larger than the diameter of lower portion 86. Therefore, insertion of dilator 88 through the bore expands the exterior diameter of shaft 82 adjacent lower portion 86. It will be appreciated that by expanding the exterior diameter of shaft 82 after cannulation, gap 32 may be substantially, if not entirely, closed, thereby stopping the flow of blood escaping from vessel 14.

As dilator 88 is tubular, it may be used for any of the desired procedures as side arm 15 of cannula 10. Additionally, cannula 80 may also be used in combination with any of sleeves 38, 54, 58, or 70.

Although the hematoma prevention apparatus and method have been described with reference to the illustrated embodiments, it is noted that variations and changes may be made, and equivalents employed herein without departing from the scope of the invention as recited in the claims.

What is claimed is:

1. A hematoma-preventing cannula assembly comprising:
   an elongated percutaneous cannula having a distal end adapted for insertion through a patient's skin and into a subcutaneous blood vessel, and a proximal end adapted for location in an extracorporeal position outside of the patient's skin; and
   an elongated sleeve positioned about a portion of said cannula with an inner end adjacent said blood vessel and extending outwardly through the patient's skin to present an outer end, said sleeve including structure defining an elongated, axially extending blood flow passageway between said inner and outer ends for permitting seepage flow of blood escaping from said vessel through said sleeve passageway and out of the patient's body in order to prevent the formation of hematomas, said sleeve presenting an inner surface engaging said cannula, said inner surface also including structure presenting at least one elongated, axially extending recess defining said passageway.

2. The assembly of claim 1, said inner surface including structure presenting a plurality of circumferentially spaced recesses defining a corresponding plurality of passageways.

3. The assembly of claim 1, said sleeve being flexible and constructed of a synthetic resin material.

4. The assembly of claim 1, said sleeve including structure presenting an elongated, axially extending, joint-defining slit along the length of said sleeve.

5. The assembly of claim 1, including an elongated, arcuate segment extending outwardly from said proximal end of said sleeve, said segment including structure defining a continuation of said blood flow passageway.

6. The assembly of claim 1, wherein said sleeve is substantially tubular.

7. The assembly of claim 1, further including a tube carried by said sleeve and having an open inlet end adjacent said inner end of said sleeve and an outer end adapted for connection to a vacuum source.

8. The assembly of claim 1, further including a tube carried by said sleeve and having an open inlet end adjacent said inner end of said sleeve and an outer end adapted for connection to an anesthetic source.

9. The assembly of claim 1, including an elongated, tubular dilator within and extending along the length of said cannula for expanding said cannula and minimizing said seepage flow of escaping blood from said vessel.

10. A method of preventing formation of a hematoma as a consequence of insertion of a percutaneous cannula through a patient's skin and into a subcutaneous blood vessel having an exterior, said method comprising the steps of:

providing an elongated percutaneous cannula having a distal end and a proximal end;

inserting said cannula through a patient's skin and positioning said distal end thereof within a subcutaneous blood vessel, with said proximal end located outside the patient's body; and draining the seepage flow of blood escaping from said blood vessel around the exterior of said cannula to a point outside the patient's body, said draining step comprising the steps of placing an elongated sleeve around said cannula which extends from a point adjacent said blood vessel exterior to an extracorporeal position outside the patient's body, said sleeve including structure defining an elongated, axially extending blood flow passageway, and causing said seepage flow of escaping blood to flow through said passageway.

11. The method of claim 10, including the step of placing said sleeve around said cannula prior to said insertion of said cannula.

12. The method of claim 10, including the step of first inserting said cannula and thereafter positioning said sleeve thereon.

13. The method of claim 10, including the step of inserting an elongated dilator into said cannula for expanding the cannula and lessening said seepage flow of escaping blood.

14. A hematoma-preventing cannula assembly comprising:

an elongated, flexible, radially expandable percutaneous cannula having a distal end adapted for insertion through a patient's skin and into a subcutaneous blood vessel, and a proximal end adapted for location in an extracorporeal position outside of the patient's skin;

a tubular dilator positioned within said cannula and radially expanding the cannula at a point adjacent said blood vessel in order to lessen the seepage flow of blood escaping from said vessel around the exterior of said cannula; and an elongated sleeve positioned about a portion of said cannula with an inner end adjacent said blood vessel and extending outwardly through the patient's skin to present an outer end, said sleeve including structure presenting at least one elongated, axially extending recess defining a blood flow passageway between said inner and outer ends for permitting seepage flow of blood escaping from said vessel through said sleeve passageway and out of the patient's body in order to prevent the formation of hematomas.

15. A hematoma-preventing cannula assembly comprising:

an elongated percutaneous cannula having a distal end adapted for insertion through a patient's skin and into a subcutaneous blood vessel, and a proximal end adapted for location in an extracorporeal position outside of the patient's skin; and an elongated sleeve positioned about a portion of said cannula with an inner end adjacent said blood vessel and extending outwardly through the patient's skin to present an outer end, said sleeve including structure defining an elongated, axially extending blood flow passageway between said inner and outer ends for permitting seepage flow of blood escaping from said vessel through said sleeve passageway and out of the patient's body in order to prevent the formation of hematomas, said sleeve including structure presenting an elongated, axially extending, joint-defining slit along the length of said sleeve for permitting positioning of said sleeve about said portion of said cannula after said cannula has been inserted through the patient's skin.

* * * * *